United States Patent
Sargeant et al.

(10) Patent No.: US 9,180,221 B2
(45) Date of Patent: *Nov. 10, 2015

(54) FUNCTIONALIZED ADHESIVE FOR MEDICAL DEVICES

(75) Inventors: Tim Sargeant, Guilford, CT (US); Robert Ahmad Hadba, Fort Worth, TX (US); Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 374 days.

This patent is subject to a terminal disclaimer.

(21) Appl. No.: 13/637,172

(22) PCT Filed: Mar. 24, 2011

(86) PCT No.: PCT/US2011/029857
§ 371 (c)(1),
(2), (4) Date: Jan. 10, 2013

(87) PCT Pub. No.: WO2011/119878
PCT Pub. Date: Sep. 29, 2011

(65) Prior Publication Data
US 2013/0098550 A1    Apr. 25, 2013

Related U.S. Application Data

(60) Provisional application No. 61/317,456, filed on Mar. 25, 2010.

(51) Int. Cl.
```
A61L 24/00    (2006.01)
A61L 15/58    (2006.01)
A61L 24/04    (2006.01)
A61L 27/14    (2006.01)
A61L 27/50    (2006.01)
A61L 31/14    (2006.01)
```

(52) U.S. Cl.
CPC ............. *A61L 24/001* (2013.01); *A61L 15/58* (2013.01); *A61L 24/04* (2013.01); *A61L 27/14* (2013.01); *A61L 27/50* (2013.01); *A61L 31/14* (2013.01)

(58) Field of Classification Search
CPC ... A61L 15/58; A61L 33/0082; A61L 24/001; A61L 24/04; A61L 27/14; A61L 27/50; A61L 31/14; C09J 187/00
USPC .............................................. 156/327, 331.6
See application file for complete search history.

(56) References Cited

U.S. PATENT DOCUMENTS

| | | | |
|---|---|---|---|
| 4,839,345 A | 6/1989 | Doi et al. | |
| 5,840,215 A | 11/1998 | Iyer et al. | |
| 8,535,477 B2 * | 9/2013 | Ladet et al. | 156/325 |
| 8,968,760 B2 * | 3/2015 | Sargeant et al. | 424/422 |
| 2005/0216054 A1 | 9/2005 | Widomski et al. | |
| 2005/0222427 A1 | 10/2005 | Sharpless et al. | |
| 2005/0281883 A1 | 12/2005 | Daniloff et al. | |
| 2006/0110782 A1 | 5/2006 | Bertozzi et al. | |
| 2007/0272122 A1 | 11/2007 | Lahann et al. | |
| 2008/0035243 A1 | 2/2008 | Breitenkamp et al. | |
| 2009/0104183 A1 | 4/2009 | Gong et al. | |
| 2009/0188602 A1 | 7/2009 | Delapierre et al. | |
| 2009/0208684 A1 | 8/2009 | Dunleavy et al. | |
| 2009/0247651 A1 | 10/2009 | Kapiamba et al. | |
| 2009/0266467 A1 | 10/2009 | Stopek et al. | |

FOREIGN PATENT DOCUMENTS

| | | |
|---|---|---|
| EP | 2106809 A2 | 10/2009 |
| WO | 2006034128 A2 | 3/2006 |
| WO | 2010095045 A1 | 8/2010 |
| WO | 2010095054 A2 | 8/2010 |

OTHER PUBLICATIONS

International Search Report corresponding to International Application No. PCT/US2011/029857, completed on May 11, 2011 and mailed on Jun. 1, 2011; 3 pages.
Raghavan, et al., "Chemical probes for profiling fatty acid-associated proteins in living cells", *Bioorganic & Medicinal Chemistry Letters*, 18 (2008), pp. 5982-5986.
Shi, et al., "The immobilization of proteins on biodegradable polymer fibers via click chemistry", *Biomaterials*, 29 (2008) pp. 1118-1126.
Haridas, et al., "Design and synthesis of triazole-based peptide dendrimers" *Tetrahedron Letters*, Science Direct, 48 (2007) pp. 4719-4722.
Cazalis, et al., "C-Terminal Site Spefici PEGylation of a Truncated Thrombomodulin Mutant with Retention of Full Bioactivity" *Bioconjugale Chem*, 15 (2004) pp. 1005-1009.
Codelli, et al. "Second-Generation Difluorinated Cyclooctynes for Copper-Free Click Chemistry", *J. AM. Chem. Soc (JACS Articles)*, 130 (2008) pp. 11486-11493.
Dirks, et al. "Preparation of biohybrid amphiphiles via the copper catalysed Huisgen [3 + 2] dipolar cycloaddition reaction", *Chem. Commun.*, (2005) pp. 4172-4174.
Sletten, et al. "A Hydrophilic Azacyclooctyne for Cu-Free Click Chemistry" *Organic Letters*, vol. 10, No. 14, (2008) pp. 3097-3099.
Baskin, et al. "Copper-free click chemistry for dynamic in vivo imaging" *PNAS*, vol. 104, No. 43, (2007), pp. 16793-16797.
Smith, et al., "Synthesis and Convenient Fictionalization of Azide-Labeled Diacylglycerol Analogues for Modular Access to Biologically Active Lipid Probes" *Bioconjugate Chemistry*, 19(9) (2008), pp. 1855-1863—Abstract Only.
European Search Report, Application No. 11760252.4 dated Jul. 27, 2015.

* cited by examiner

*Primary Examiner* — Tae H Yoon

(57) ABSTRACT

A method for adhering a medical device to biological tissue includes adhering an adhesive composition having a plurality of reactive members of a specific binding pair to tissue which has a plurality of complementary reactive members of the specific binding pair via click chemistry.

30 Claims, No Drawings

FUNCTIONALIZED ADHESIVE FOR MEDICAL DEVICES

CROSS-REFERENCE TO RELATED APPLICATIONS

This application is a U.S. National Stage Application filed under 35 U.S.C. §371(a) of International Application No. PCT/US2011/029857 filed Mar. 24, 2011, which claims the benefit of and priority to U.S. Provisional Patent Application Ser. No. 61/317,456 filed Mar. 25, 2010, the entire contents of which are incorporated by reference herein.

BACKGROUND

1. Technical Field

The present disclosure relates to adhesive modalities for repair of biological tissues.

2. Related Art

Medical adhesives or "tissue glue" have much potential in medicine. Certain adhesive materials are known which may be used to adhere tissue such as skin. For example, cyanoacrylate adhesives been used to bond tissue. In addition to cyanoacrylate adhesives, other types of materials have been reported to adhere to skin. For example, U.S. Pat. No. 4,839,345 to Doi et al. reports a hydrated crosslinked protein adhesive gel that is used as a cataplasm or cosmetic mask that will externally adhere to skin but can be removed and then re-adhered to the skin. Other crosslinked protein hydrogels have been reported to serve as a proteinaceous substrate to deliver therapeutic agents such as enzymes or drugs through skin or mucous membranes. Still other materials have been used as hemostatic agents to stop or prevent bleeding. For example, mixtures of fibrinogen and thrombin such as TISSEEL® sealant available from Baxter International, Inc. or BERIPLAST-P® hemostatic agent or sealant available from Aventis Behring, have been used in vascular surgery to seal tissue such as blood vessels and thus prevent blood leakage.

The use of medical gels such as hydrogels can be advantageous due to the physico-chemical properties of the hydrogels. Hydrogels typically have excellent compatibility with human and animal tissue. Physically cross linked hydrogels can withstand attack by body fluids, blood, urine and other bodily secretions without significant damage. Many are typically non-adherent to tissue, do not have an affinity for binding to proteins and do not have cell adsorption. Hydrogels are typically non-thrombogenic. These characteristics have been utilized, e.g., for prevention of adhesions after surgery. The ability of hydrogels to act as bulking agents has been utilized in connection with treatment of gastroesophageal reflux disease (GERD), urinary incontinence, fecal incontinence and sterilization of mammals. Hydrogels have also been used to create a matrix in the treatment of damaged cartilage.

Click chemistry is a popular term for reliable reactions that make it possible for certain chemical building blocks to "click" together and form an irreversible linkage. See, e.g., US Pub. No. 2005/0222427. In the case of azide-alkyne click chemistry, the reactions may be catalyzed or uncatalyzed. For example, copper-free click chemistry was recently developed by Bertozzi and colleagues using difluorinated cyclooctyne or DIFO that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, US Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyazacyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions.

It would be advantageous to be able to secure a bifunctional adhesive layer having one functionality which provides selective attachment to a target site within the body and another functionality which provides an adhesive surface for selective attachment of a medical device to the adhesive layer at the target site.

SUMMARY

A method for adhering a medical device to biological tissue is provided which includes providing a bifunctional adhesive composition having a plurality of reactive members of a first specific binding pair and a plurality of reactive members of a second specific binding pair; providing tissue with a plurality of complementary reactive members of the first specific binding pair; contacting the adhesive composition with the biological tissue, wherein upon contact of the reactive members of the first specific binding pair with the complimentary reactive members of the first specific binding pair on the tissue, covalent bonds are formed between the reactive members and the complementary reactive members of the first specific binding pair, thus adhering the adhesive to the tissue; providing a medical device having a plurality of complementary reactive members of the second specific binding pair; contacting the medical device with the adhesive, wherein upon contact of the reactive members of the second specific binding pair with the complimentary reactive members of the second specific binding pair on the device, covalent bonds are formed between the reactive members and the complementary reactive members of the second specific binding pair, thus adhering the device to the adhesive composition.

A method for adhering a medical device to biological tissue is provided which includes providing an adhesive composition having a plurality of reactive members of a specific binding pair; providing tissue with a plurality of complementary reactive members of the specific binding pair; contacting the adhesive composition with the biological tissue, wherein upon contact of the reactive members of the specific binding pair with the complimentary reactive members of the specific binding pair on the tissue, covalent bonds are formed between the reactive members and the complementary reactive members of the specific binding pair, thus adhering the adhesive to the tissue; providing a medical device having a plurality of complementary reactive members of the specific binding pair; contacting the medical device with the adhesive, wherein upon contact of the reactive members with the complimentary reactive members of the specific binding pair on the device, covalent bonds are formed between the reactive members and the complementary reactive members of the specific binding pair, thus adhering the device to the adhesive composition.

A method for adhering a medical device to biological tissue includes adhering an adhesive composition having a plurality of reactive members of a specific binding pair to tissue which has a plurality of complementary reactive members of the specific binding pair via click chemistry. The adhesive composition contains additional reactive members of a specific bind pair which may be the same or different than the specific binding pair associated with the tissue. The medical device is adhered to the tissue through the adhesive composition via covalent bonds formed by click chemistry between the members of the specific binding pair associated with the device and the members of the specific bind pair associated with the adhesive composition. A bifunctional bioadherent composition includes a substrate having a plurality of reactive members of a first specific binding pair and a plurality of reactive members of a second specific binding pair. The reactive members of the first specific binding pair are capable of forming covalent bonds with a plurality of complementary reactive members of the first specific binding pair via a click chemistry reaction. The reactive members of the second specific binding pair are capable of forming covalent bonds with a plurality of complementary reactive members of the second specific binding pair via a click chemistry reaction.

A bifunctional bioadherent composition is provided which includes a substrate having a plurality of reactive members of a first specific binding pair and a plurality of reactive members of a second specific binding pair, said reactive members of the first specific binding pair being capable of forming covalent bonds with a plurality of complementary reactive members of the first specific binding pair via a reaction selected from a Huisgen cycloaddition, a Diels-Alder reaction, and a thiol-alkene reaction, said reactive members of the second specific binding pair being capable of forming covalent bonds with a plurality of complementary reactive members of the second specific binding pair via a reaction selected from a Huisgen cycloaddition, a Diels-Alder reaction, and a thiol-alkene reaction.

A kit is provided which includes a bifunctional bioadherent composition including a substrate having a plurality of reactive members of a first specific binding pair and a plurality of reactive members of a second specific binding pair, said reactive members of the first specific binding pair being capable of forming covalent bonds with a plurality of complementary reactive members of the first specific binding pair via a reaction selected from a Huisgen cycloaddition, a Diels-Alder reaction, and a thiol-alkene reaction, said reactive members of the second specific binding pair being capable of forming covalent bonds with a plurality of complementary reactive members of the second specific binding pair via a reaction selected from a Huisgen cycloaddition, a Diels-Alder reaction, and a thiol-alkene reaction; and at least one applicator adapted to deliver the bifunctional bioadherent composition to biological tissue. The kit may also include a medical device having a plurality of complementary reactive members of the second specific binding pair; wherein upon contact of the reactive members of the second specific binding pair with the complimentary reactive members of the second specific binding pair on the device, covalent bonds are formed between the reactive members and the complementary reactive members of the second specific binding pair.

DETAILED DESCRIPTION

A surgical adhesive system for medical devices such as scaffolds, adhesion barriers, patches, matrices, plugs, bandages, mesh and other implants such as prosthetics including, e.g., joint prostheses, dental implants and cosmetic implants, and biological tissue is provided. Such devices are covalently bonded to a layer which is itself covalently bonded to biological tissue utilizing reactive members and complementary reactive members of specific binding pairs via click chemistry. In this manner, an adhesive layer forms a bridge between tissue at a surgical target site and a medical device. Efficient and effective repair of exteriorly and interiorly disposed wounds or defects in a patient such as those which may occur on bodily tissue such as skin, bone, cartilage, ligament, or in hollow organs such as the gastrointestinal tract is provided by a surgical adhesive system herein at the site of the wound or defect (collectively "the target site"). The reactive members are contained in a substrate which forms an adhesive layer and are designed to have an affinity for one or more complementary reactive members of a specific binding pair located on or in tissue cells at the target site which causes the reactive members and thus, the substrate, to bind securely to the tissue cells. In addition, the substrate includes reactive members of a specific binding pair which may be the same or different than the specific binding pair associated with tissue. The reactive members covalently bind to complementary reactive members of the specific binding pair which are located on and/or in a medical device. After the adhesive layer binds to the tissue, the medical device is then brought into contact with the adhesive layer, covalent bonds form between the members of the specific binding pair, and the device is adhered to the tissue site.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

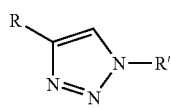

where R is a polymeric backbone and R' is a component of a biologic tissue. Alternatively, R is a component of a biologic tissue and R' is a polymeric backbone.

The Diels-Alder reaction combines a diene (a molecule with two alternating double bonds) and a dienophile (an alkene) to make rings and bicyclic compounds. Examples include:

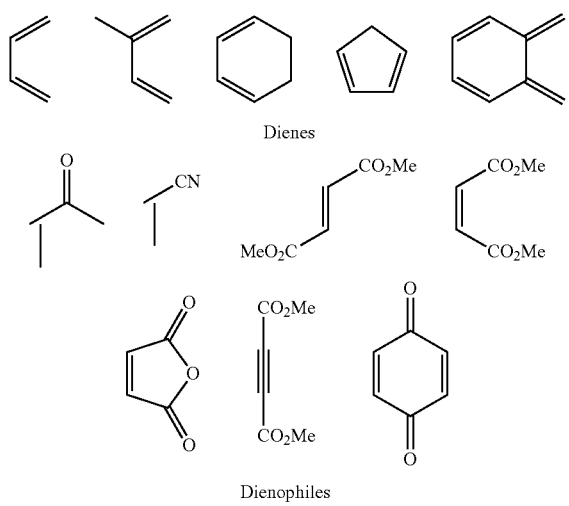

The thiol-alkene (thiol-ene) reaction is a hydrothiolation, i.e., addition of RS—H across a C═C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

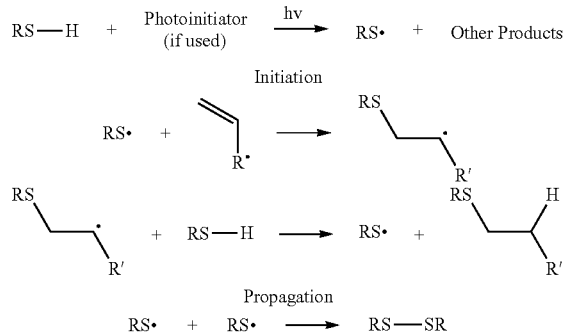

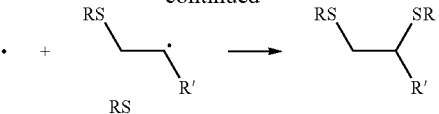

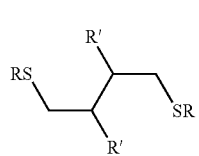

Termination

In accordance with the disclosure herein, a bifunctional substrate is provided with a plurality of reactive members of a specific binding pair attached on the surface and/or in the substrate. The substrate may be a medical gel which is sprayed on to tissue or applied as a preformed layer. The substrate may be a non-gel polymeric composition which is also sprayed on to tissue or applied as a preformed layer.

Gels used in medicine such as hydrogels are well-known. As used herein, unless otherwise specified, "attached to the surface of the gel" or "attached on the surface of the gel" or "located on the gel" is intended to include attachment to molecules which are precursors of a gel before it coagulates. When the reactive members of a medical gel are contacted with biological tissue containing complementary reactive members of a specific binding pair, covalent attachment occurs, thus adhering the gel to the tissue. In embodiments, the reactive members may be either a dipolarophile or a 1,3 dipolar compound depending on which complement is applied to the target tissue or the medical gel. For example, if a dipolarphile is located on the gel, the 1,3 dipolar compound will be located on the tissue. If a dipolarphile is located on the tissue, the 1,3 dipolar compound will be located on the gel. In embodiments, the Diels-Alder members of a specific binding pair may be either a diene or a dienophile depending on which complement is applied to the target tissue or the medical gel. For example, if a diene is located on the gel, the dienophile can be located on the tissue. If a diene is located on the tissue, the dienophile can be located on the gel. In embodiments, the thiol-ene members of a specific binding pair may be either a thiol or an alkene depending on which complement is applied to the target tissue or the gel. For example, if a thiol is located on the gel, the alkene can be located on the tissue. If a thiol is located on the tissue, the alkene can be located on the gel.

The bifunctional substrate, e.g., gel, contains reactive members which may be the same or different than the reactive members of the specific binding pair which results in covalent attachment to tissue. In the case where the reactive pairs are the same, left over or unreacted reactive members are available to covalently bind to complementary reactive members of the specific binding pair which, in addition to being present on and/or in tissue are also located on and/or in a medical device, thus causing the medical device to adhere to the gel. In the case where the reactive members are different than the reactive members of the specific binding pair which result in bonding of the gel to complementary reactive members on and/or in the tissue (the first specific binding pair), the different reactive members are members of a second specific binding pair and will covalently bond to complementary reactive members of the second binding pair which are located on and/or in the medical device, thus causing the device to adhere to the gel.

After the gel is applied to tissue and covalently bonded thereto and the available reactive members of the gel are contacted with a medical device containing complementary reactive members of a specific binding pair (either the first or second binding pair), covalent attachment occurs, thus adhering the device to the tissue through the gel. In embodiments, the reactive members of the first or second binding pair may be either a dipolarophile or a 1,3 dipolar compound depending on which complement is applied to the gel or the device. For example, if a dipolarphile is located on and/or in the device, the 1,3 dipolar compound will be located on and/or in the gel. If a dipolarphile is located on and/or in the gel, the 1,3 dipolar compound will be located on and/or in the device. In embodiments, the Diels-Alder members of a first or second specific binding pair may be either a diene or a dienophile depending on which complement is applied to the gel or the device. For example, if a diene is located on and/or in the device, the dienophile can be located on and/or in the gel. If a diene is located on and/or in the gel, the dienophile can be located on and/or in the device. In embodiments, the thiol-ene members of a first or second specific binding pair may be either a thiol or an alkene depending on which complement is applied to the gel or the device. For example, if a thiol is located on and/or in the device, the alkene can be located on and/or in the gel. If a thiol is located on and/or in the gel, the alkene can be located on and/or in the device.

The substrate may be biocompatible and absorbable or biocompatible and non-absorbable. In embodiments, the reactive members are attached directly to the polymeric backbone of a substrate. In embodiments, the reactive members are attached to the polymeric backbone via a cross-linker. Cross-linkers are discussed below. For example, hydrogels can be formed, e.g., when an organic polymer, also referred to herein as precursor molecules which form the gel, which can be natural or synthetic, is set or at least partially solidified to create a three-dimensional open-lattice structure that entraps molecules of water or other solutions to form a gel. Hydrogels have an affinity for water and typically swell in water, but do not necessarily dissolve in water. Solidification can occur by aggregation, coagulation, hydrophobic interactions, crosslinking, or similar means. In certain embodiments, hydrogels are formed by polymerization and crosslinking of a hydrophilic monomer in an aqueous solution to cause the solution to gel. In embodiments, the hydrogel is composed of 85% water, to which can be added any salt or adjuvant.

Hydrogels may be organic gels or inorganic gels. Organic gels from which the hydrogel of the invention can be selected include, by way of example and not by way of limitation, gels formed from polysaccharides and mucopolysaccharides including, but not limited to hyaluronic acid, dextran, heparin sulfate, chondroitin sulfate, agar, starch, and alginate; proteins, including but not limited to, fibronectin, gelatin, collagen, fibrin, chitosan, chitin, pectins, albumin, ovalbumin, and polyamino acids; collagen-hydroxyethyl-methacrylate (HEMA); polyphosphazines; polyphosphoesters; polyethylene glycol; polyethylene oxide; polyvinyl alcohol; polyvinylpyrrolidone; polyethyloxazoline; poly(ethylene oxide-co-propylene oxide) block copolymers; PGA-PEG-PGA block copolymers; PGA-PEG diblock copolymers; acrylates, including but not limited to diacrylates, oligoacrylates, methacrylates, dimethacrylates and oligomethacrylates; PEG-oligoglycolylacrylates; polyacrylonitriles (PAN); carboxy alkyl celluloses, including but not limited to carboxymethyl cellulose; partially oxidized cellulose; biodegradable polymers including but not limited to polymers and oligomers of glycolide, lactide, polyesters of α-hydroxy acids, including lactic acid and glycolic acid, such as the poly(α-hydroxy) acids including poly(glycolic acid), poly(DL-lactic acid), poly(L-lactic acid), and terpolymers of DL-lactide and glycolide; ε-caprolactone and ε-caprolactone copolymerized with polyesters; polylactones and polycaprolactones including poly(ε-caprolactone), poly(δ-valerolactone) and poly(γ-butyrolactone); polyanhydrides; polyorthoesters; polydioxanone; and other biologically degradable polymers that are non-toxic or are present as metabolites in the body; as well as non-degradable polymers such as styrene and acrolein.

Collagen-hydroxyethyl methacrylate (HEMA) hydrogel polymer is commonly formed from a gelled and crosslinked hydrophilic monomer solution to form a three dimensional polymeric meshwork anchoring macromolecules. Crosslinking of the hydrophilic monomer solution can be accomplished by free radical polymerization of hydrophilic monomers, such as hydroxyethyl methacrylate (HEMA). Hydrogel polymers formed by free radical polymerization of monomer solutions require crosslinking to form the three dimensional network to gel the aqueous solution. HEMA monomer solutions typically can be crosslinked to gel by dimethacrylates, such as ethylene glycol dimethacrylate, or poly(ethylene glycol) dimethacrylate, although other crosslinking agents such as n,n'-methylene bisacrylamide or divinyl benzene, can also be used during polymerization to modify the hydrogel. A wide variety of other hydrophilic monomers may also be suitable for purposes of the invention.

Inorganic gels include, by way of example and not by way of limitation, silica, alumina, and ferric oxide.

Bulk and cellular hydrogels may be prepared by covalent cross linking or physical cross linking of the hydrogel molecules. Thus, covalent cross linking, also known as chemical cross linking, includes the use of multi-functional reactive chemical molecules such as aldehydes, maleic acid, dimethylurea, diisocyanates, boric acid, and the like, and also the use of ionizing radiation, ultraviolet light, and the like, while physical cross linking methods, also known as reversible cross linking, includes cross linking through crystallites, hydrogen bonding and complexing agents such as calcium, magnesium, iron, titanium, aluminum, manganese, and copper, to name a few. Physical cross linking through formation of crystallites in, e.g., polyvinyl alcohols, chitosan and the like, using, for example, partial freeze-drying, repeated freezing and thawing, low temperature crystallization, physical cross linking induced by the presence of aqueous solutions of organic compounds, salts, acids and bases and the like.

The substrate may also be constructed from biocompatible absorbable polymers or biocompatible non-absorbable polymers that may not be considered to be gels. Examples of suitable polymers include polycarbonates, polyolefins, polymethacrylates, polystyrenes, polyamides, polyurethanes, poly(ethylene terephthalate), poly(lactic acid), poly(glycolic acid), polyhydroxbutyrate, polydioxanones (e.g., 1,4-dioxanone), δ-valerolactone, 1-dioxepanones (e.g., 1,4-dioxepan-2-one and 1,5-dioxepan-2-one), polyesters, poly(ethylene glycol), poly(ethylene oxides), polyacrylamides, cellulose esters, fluoropolymers, vinyl polymers, silk, collagen, alginate, chitin, chitosan, hyaluronic acid, chondroitin sulfate, glycosaminoglycans, poly(hydroxyethyl methacrylate), polyvinylpyrrolidone, poly(vinyl alcohol), poly(acrylic acid), polyacetate, polycaprolactone, poly(propylene, glycol)s, poly(amino acids), copoly(ether-esters), poly(alkylene oxalates), polyamides, poly(iminocarbonates), polyoxaesters, polyorthoesters, polyphosphazenes, polypeptides and copolymers, block copolymers, homoploymers, blends and combinations thereof.

The substrate may be dissolved in a solvent and applied to the target site by spraying, painting, pouring or by any other method known to those skilled in the art. Alternatively, the substrate may be preformed as a layer which is then placed onto the target site. Methods of forming layers are well-known such as solvent casting.

In the present application, the term "bioresorbable", "bioabsorbable" and "absorbable" are used interchangeably and are intended to mean the characteristic according to which a medical device and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

Many of the above described examples of polymers do not contain functional groups in their molecules. In embodiments, the reactive members are attached to the substrate by surface modification techniques such as plasma treatment, silane coupling treatment and acid sensitization. Surface activation of the substrate can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, Ba(OH)$_2$, Mg(OH)$_2$, NaOH, KOH, Na$_2$CO$_3$, Ca(OH)$_2$ and the weak bases, such as for example NH$_4$OH and the ammines such as methylamine, ethylamine, diethylamine and dimethylamine. Acids suitable for surface hydrolysis treatments can be chosen, for example, from among HCl, HClO$_3$, HClO$_4$, H$_2$SO$_3$, H$_2$SO$_4$, H$_3$PO$_3$, H$_3$PO$_4$, HI, HIO$_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a gas, for example air, Ar, O$_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the polymeric substrate. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—CH$_2$—CH$_2$—COOH groups. Suitable surface activation techniques are disclosed in U.S. Pat. No. 6,107,453, the entire disclosure of which is incorporated herein by this reference.

During manufacture of polymers, pendant functional groups can be incorporated into the polymer backbone by, e.g., copolymerization with functionalized monomer such as lactones, cyclic carbonates and morpholine-2,5-diones. The azido group, N$_3$ is a nucleophilic group that will exchange with other nucleophilic groups, e.g., —OH, —NH$_2$ and halogens (Br, Cl, or I). For example, 1,3-dipolar compounds may be conjugated to aliphatic polyesters, by copolymerizing, e.g., ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with ZnEt$_2$ as a catalyst. See, Shi et al., Biomaterials, 29 (2008)1118-1126. Azide functionalized polystyrene is synthesized using atom transfer radical polymerization and subsequent modification with azidotrimethylsilane and tetrabutylammonium fluoride. See, Dirks, et al., Chem. Comm., (2005) 4172-4174. Azides may be incorporated onto methacrylates, e.g., 3-azidopropyl methacrylate which is copolymerized to a block copolymer. Diels-Alder functionalities and thiol-ene functionalities are likewise incorporated into polymers herein.

Biological tissue may be provided with complementary reactive members of a specific binding pair by conjugation to various components of tissue such as proteins, lipids, oligosaccharides, oligonucleotides, glycans, including glycosaminoglycans. In one embodiment, the complementary reactive members are attached directly to components of the tissue. In embodiments, the complementary reactive members are attached to components of the tissue via a linker. In either case, situating the complementary reactive members on the tissue can be accomplished by suspending the complementary reactive members in a solution or suspension and applying the solution or suspension to the tissue such that the complementary reactive members bind to a target. The solution or suspension may be poured, sprayed or painted onto the tissue, whereupon the complementary reactive members are incorporated into the tissue.

1,3-Dipolar compounds can be incorporated into proteins, lipids, oligosaccharides, oligonucleotides and glycans using, e.g., metabolic machinery, covalent inhibitors and enzymatic transfers. For example, an azido group, N$_3$, can be applied at the N-terminus of proteins or peptides using azidoacetyl chloride. See, e.g., Haridas, et al., Tetrahedron Letters 48 (2007) 4719-4722. The azido group is a nucleophilic group that will exchange with other nucleophilic groups, e.g., —OH, —NH$_2$ and halogens (Br, Cl, or I). NaN$_3$ is an azidizing agent which is capable of aziding proteins by simply contacting the proteins with a 10 times molar excess of NaN$_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive group. Reactive groups (as opposed to reactive members or complementary reactive members herein) are those to which an activated PEG molecule may be bound (e.g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate), in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with propargylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16-carbon alkynyl-dimethylphosphonate. See, e.g., Raghavan et al., Bioorg. Med. Chem. Lett., 18 (2008) 5982-5986. As above, PEGylation may be used for adding dipolarophile groups to peptides and proteins and is suitable for use herein. Diels-Alder functionalities and thiol-ene functionalities are likewise attached to proteins, lipids, oligosaccharides, oligonucleotides and glycans.

The complementary reactive members may be also attached to biological tissue or the medical gel via a linker. In certain embodiments, the linker is or includes a ligand which bears a complementary reactive member. The ligand binds to a desired target on the tissue and thus provides a vehicle for transporting and indirectly binding the complementary reactive member to the tissue. The ligand herein is any molecule or combination of molecules which demonstrates an affinity for a target. Examples of ligands include nucleic acid probes, antibodies, hapten conjugates, and cell adhesion peptides such as RGD. The mechanisms involved in obtaining and using such ligands are well-known. In embodiments, complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to complementary reactive members are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides), are conjugated or linked to complementary reactive members in the manners described above. In addition, complementary reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the complementary reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl)cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and $N,N^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of reactive members to the substrate functionalizes the substrate such that upon exposure to their complementary reactive members which are situated on tissue, they are activated and form covalent bonds, thus adhering the substrate to the tissue. In one embodiment, a linker between the product of the reactive members and complementary reactive members is degradable by, e.g., hydrolysis or enzymatic action. In this manner, the substrate can be removable after a period of time. The degradable linkage may be chelates or chemically or enzymatically hydrolyzable or absorbable. Illustrative chemically hydrolyzable degradable linkages include polymers, copolymers and oligomers of glycolide, d,l-lactide, l-lactide, caprolactone, dioxanone, and trimethylene carbonate. Illustrative enzymatically hydrolyzable biodegradable linkages include peptidic linkages cleavable by metalloproteinases and collagenases and chitosan cleavable by lysozyme. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The ligand solution and substrate can be sterilized by any known method, e.g., irradiation, ethylene oxide, filtration in sterile conditions on a 0.22 um filter and the like.

Adhesive substrates herein may be used in a variety of applications. In one embodiment, the substrate is an uncured liquid, functionalized with a plurality of reactive members of a binding pair, which is applied and cured as a layer on surfaces of external or internal organs or tissues which were pretreated with the complementary reactive member as described above. The target tissue is pretreated by spraying, painting or pouring a solution or suspension containing the complementary reactive members of a binding pair on to the tissue. Ligands associated with the complementary reactive members bind to their predetermined targets on the tissue, thereby anchoring the complementary reactive members on the tissue. The uncured functionalized liquid substrate is sprayed over, e.g., a defect on the tissue where it cures while simultaneously, the reactive members and complementary reactive members of the specific binding pair react specifically together to form covalent bonds, providing adhesion between the tissue and the curing or cured substrate. In embodiments, the substrate is cured prior to application to pretreated tissue and then draped over or otherwise contacted with the target site to allow the covalent bond forming reaction to occur with consequent covalent bonding and adherence. In embodiments, two opposing tissue surfaces are pretreated and functionalized, and functionalized substrate added to form bonds to both opposing surfaces.

After the adhesive substrate is applied to the target site, a medical device is then brought into contact with the substrate, and covalent bonds form between the available reactive members in and/or on the substrate and the complementary reactive members located on and/or in the device, thus causing adhesion of the device to the target site. Therapeutic cells or viruses can be made to adhere to a target site in a similar manner, i.e., complementary reactive members can be located or displayed on the surface of cells or virus coat which form covalent bonds with the reactive members in and/or on the substrate. In embodiments, a medical device such as a scaffold can be loaded with cells, e.g., chondrocytes, stem cells and the like which have been functionalized with complementary reactive members which covalently adhere to the substrate on contact. In embodiments, the cells can be made to adhere to the device by providing the device with reactive members of a specific binding pair that covalently bond to complementary reactive members of the specific binding pair that have been incorporated into the device. For example, a scaffold will bind cells such as chondrocytes by virtue of cell immobilization functionality imparted by a click chemistry reaction. In the case of cartilage repair, e.g., the target site can be prepared, the adhesive substrate applied, micofracture perfomed, and then the scaffold is applied.

In addition, a medicinal agent incorporating complementary reactive members could be adhered to a target site via an adhesive substrate layer. The term "medicinal agent", as used herein, is meant to be interpreted broadly and includes any substance or mixture of substances which may have any clinical use in medicine. Thus, medicinal agents include drugs, enzymes, proteins, peptides, glycoproteins, or diagnostic agents such as releasable dyes which may have no biological activity per se. Examples of classes of medicinal agents that can be used include antimicrobials, analgesics, antipyretics, anesthetics, antiepileptics, antihistamines, anti-inflammatories, anti-clotting agents, cardiovascular drug, diagnostic agents, sympathomimetics, cholinomimetics, anti-muscarinics, antispasmodics, hormones, growth factors, muscle relaxants, adrenergic neuron blocks, anti-neoplastics, immunosuppressants, gastrointestinal drugs, diuretics, steroids and enzymes. It is also intended that combinations of medicinal agents can be used. Those skilled in the art are familiar with various techniques for incorporating a medicinal agent into a coating to allow rapid or sustained release of the medicinal agent.

Some applications include using the adhesive substrate to bind tissue together either as an adjunct to or as a replacement of sutures, staples, tapes and/or bandages. In another application, the substrate may be used to prevent post-surgical adhesions. In this application, the substrate, functionalized with a reactive member of a binding pair, is applied and cured as a layer on surfaces of internal organs or tissues which were pretreated with a complementary reactive member of the binding pair as described above. An adhesion barrier functionalized with complementary reactive members will then adhere to the substrate via covalent bond formation to prevent formation of adhesions at a surgical site as the site heals. In another application, the functionalized substrate may be used to attach pretreated skin grafts and to position pretreated tissue flaps or free flaps during reconstructive surgery. In still another application, the functionalized substrate may be used to close pretreated gingival flaps in periodontal surgery. Additional applications include sealing tissues with, e.g., functionalized pledgets or bandages to prevent or control blood or other fluid leaks at suture or staple lines as well as to prevent or control air leaks in the pulmonary system.

A substrate may be injected percutaneously by direct palpation. The substrate may also be injected through a catheter or needle with fluoroscopic, sonographic, computed tomography, magnetic resonance imaging or other type of radiologic guidance. This would allow for placement or injection of the substrate formulation and subsequent functionalized medical device either by vascular access or percutaneous access to specific organs or other tissue regions in the body.

Techniques of tissue engineering employing functionalized medical scaffolds can be used to create alternatives to prosthetic materials currently used in craniomaxillofacial surgery, as well as formation of organ equivalents to replaced diseased, defective, or injured tissues. To form a scaffold made from, e.g., a hydrogel containing the cells, a functionalized polymer solution is mixed with the cells to be implanted to form a suspension. Then the target site is pretreated with an adhesive layer as described herein. The reactive members in the adhesive layer bond to the complementary members supplied to the tissue and those in the scaffold thus adhering the scaffold to a target site. In embodiments, a functionalized gel is injected or poured into a mold, where it crosslinks to form a semi-solid hydrogel of the desired anatomical shape having cells dispersed therein which then may be implanted in a pretreated target area in a patient. The hydrogel may be produced, for example, by cross-linking a polysaccharide polymer by exposure to a monovalent cation. Other polymers capable of forming functionalized hydrogels as described above may be used as disclosed herein. In the embodiments where the functionalized polymer is crosslinked by contact with a crosslinking agent, the strength of the crosslink may be increased or reduced by adjusting the concentration of the polymer and/or crosslinking agent.

Further, combinations in accordance with this disclosure, e.g., a functionalized medical device having complementary reactive members of a specific binding pair and functionalized substrate containing reactive members of the specific binding pair, may be injected through a laparoscope or thoracoscope to any intraperitoneal or extraperitoneal or thoracic organ.

A kit is provided which includes a bifunctional bioadherent composition including a substrate having a plurality of reactive members of a first specific binding pair and a plurality of reactive members of a second specific binding pair, the reactive members of the first specific binding pair being capable of forming covalent bonds with a plurality of complementary reactive members of the first specific binding pair via a reaction selected from a Huisgen cycloaddition, a Diels-Alder reaction, and a thiol-alkene reaction, said reactive members of the second specific binding pair being capable of forming covalent bonds with a plurality of complementary reactive members of the second specific binding pair via a reaction selected from a Huisgen cycloaddition, a Diels-Alder reaction, and a thiol-alkene reaction. The kit may include at least one applicator for delivering the bifunctional bioadherent composition to biological tissue, e.g., a pump or pneumatic sprayer. The kit may also include a medical device having a plurality of complementary reactive members of the second specific binding pair. The kit may optionally include a container which contains a catalyst for causing the reactive members of a specific binding pair to bind with the complementary reactive members of the specific binding pair. The catalyst may be a solution of metal such as copper. In embodiments, the kit contains a microwave or ultraviolet radiation generator.

Other aspects of the invention are defined in the following clauses:

Clause 1. A bifunctional bioadherent composition which comprises a substrate having a plurality of reactive members of a first specific binding pair and a plurality of reactive members of a second specific binding pair, said reactive members of the first specific binding pair being capable of forming covalent bonds with a plurality of complementary reactive members of the first specific binding pair via a reaction selected from a Huisgen cycloaddition, a Diels-Alder reaction, and a thiol-alkene reaction, said reactive members of the second specific binding pair being capable of forming covalent bonds with a plurality of complementary reactive members of the second specific binding pair via a reaction selected from a Huisgen cycloaddition, a Diels-Alder reaction, and a thiol-alkene reaction.

Clause 2. The bifunctional bioadherent composition according to clause 1 wherein the members of the specific binding pair are alkynes and azides.

Clause 3. The bifunctional bioadherent composition according to clause 1 or 2 wherein the substrate includes a hydrogel made of a polymer selected from the group consisting of polysaccharides, mucopolysaccharides, polyaminoacids, proteins, collagen-hydroxyethyl methacrylate (HEMA), polyphosphazines, polyphosphoesters, poly(ethylene glycol), poly(ethylene oxide), poly(vinyl alcohol), polyvinylpyrrolidone, polyethyloxazoline, poly(ethylene oxide-co-propylene oxide) block copolymers, PGA-PEG-PGA block copolymers, PGA-PEG diblock copolymers, acrylates, PEG-oligoglycolylacrylates, polyacrylonitriles (PAN), carboxy alkyl celluloses, poly($\alpha$-hydroxy) acids, polylactones, polycaprolactones, polyanhydrides, polyorthoesters, polydioxanone, styrene, acrolein and copolymers, block copolymers, homoploymers, blends and combinations thereof.

Clause 4. The bifunctional bioadherent composition according to clause 1 or 2 wherein the substrate includes a polymer selected from the group consisting of polycarbonates, polyolefins, polymethacrylates, polystyrenes, polyamides, polyurethanes, poly(ethylene terephthalate), poly(lactic acid), poly(glycolic acid), polyhydroxbutyrate, polydioxanones (e.g., 1,4-dioxanone), $\delta$-valerolactone, 1,dioxepanones (e.g., 1,4-dioxepan-2-one and 1,5-dioxepan-2-one), poly(phosphazine), polyesters, polyacrylamides, cellulose esters, fluoropolymers, vinyl polymers, silk, collagen, chitin, chitosan, chondroitin sulfate, glycosaminoglycans, poly(hydroxyethyl methacrylate), polyvinylpyrrolidone, poly(acrylic acid), polyacetate, polycaprolactone, poly(propylene glycols), poly(amino acids), copoly(ether-esters), poly(alkylene oxalates), poly(iminocarbonates), polyoxaesters, polyorthoesters, polyphosphazenes, polypeptides and copolymers, block copolymers, homoploymers, blends and combinations thereof.

Clause 5. The bifunctional bioadherent composition according to any one of clauses 1, 2 and 4 wherein the substrate is a liquid.

Clause 6. The bifunctional bioadherent composition according to any one of clauses 1-4 wherein the substrate is a preformed layer.

Clause 7. A kit comprising a bifunctional bioadherent composition including a substrate having a plurality of reactive members of a first specific binding pair and a plurality of reactive members of a second specific binding pair, said reactive members of the first specific binding pair being capable of forming covalent bonds with a plurality of complementary reactive members of the first specific binding pair via a reaction selected from a Huisgen cycloaddition, a Diels-Alder reaction, and a thiol-alkene reaction, said reactive members of the second specific binding pair being capable of forming covalent bonds with a plurality of complementary reactive members of the second specific binding pair via a reaction selected from a Huisgen cycloaddition, a Diels-Alder reaction, and a thiol-alkene reaction; and at least one applicator adapted to deliver the bifunctional bioadherent composition to biological tissue.

Clause 8. The kit according to clause 7 further comprising a medical device having a plurality of complementary reactive members of the second specific binding pair; wherein upon contact of the reactive members of the second specific binding pair with the complimentary reactive members of the second specific binding pair associated with the device, covalent bonds are formed between the reactive members and the complementary reactive members of the second specific binding pair.

Clause 9. The kit according to clause 7 or 8 wherein the substrate is a liquid.

Clause 10. The kit according to clause 7 or 8 wherein the substrate is a preformed layer.

Clause 11. The kit according to any one of clauses 7-10 wherein the medical device is selected from the group consisting of scaffold, adhesion barrier, patche, matrix, plug, bandage, mesh and prosthetic device.

It should be understood that variations can be made to the above embodiments that are with the purview of ordinary skill in the art. For example, other click chemistry reactions are suitable for use herein, e.g., staudinger reaction of phosphines with alkyl azides. Although the substrate is mainly described as being applied to the tissue and then a device is applied to the substrate, it is contemplated that the substrate may first be applied to the device and then contacted with tissue. Accordingly, those skilled in the art can envision modifications which are included within the scope of the claims that are not expressly set forth herein.

What is claimed is:

1. A method for adhering a medical device to biological tissue comprising:
   providing a bifunctional adhesive composition having a plurality of reactive members of a first specific binding pair and a plurality of reactive members of a second specific binding pair;
   providing tissue with a plurality of complementary reactive members of the first specific binding pair;
   contacting the bifunctional adhesive composition with the biological tissue, wherein upon contact of the reactive members of the first specific binding pair associated with the bifunctional adhesive with the complimentary reactive members of the first specific binding pair associated with the tissue, covalent bonds are formed between the reactive members and the complementary reactive members of the first specific binding pair, thus adhering the bifunctional adhesive to the tissue;
   providing a medical device having a plurality of complementary reactive members of the second specific binding pair;
   contacting the medical device with the bifunctional adhesive, wherein upon contact of the reactive members of the second specific binding pair associated with the bifunctional adhesive with the complimentary reactive members of the second specific binding pair associated with the medical device, covalent bonds are formed between the reactive members and the complementary reactive members of the second specific binding pair, thus adhering the medical device to the biological tissue via the bifunctional adhesive composition.

2. The method for adhering a medical device to biological tissue according to claim 1 wherein the members of the first specific binding pair bind to one another via a reaction selected from the group consisting of Huisgen cycloaddition reaction, a Diels-Alder reaction and a thiol-ene reaction and the members of the second specific binding pair bind to one another via a reaction selected from the group consisting of Huisgen cycloaddition reaction, a Diels-Alder reaction and a thiol-ene reaction.

3. The method for adhering a medical device to biological tissue according to claim 2 wherein the members of the first specific binding pair are alkynes and azides.

4. The method for adhering a medical device to biological tissue according to claim 3 wherein the reactive member of the first specific binding pair is an alkyne and the complementary reactive member of the first specific binding pair is an azide.

5. The method for adhering a medical device to biological tissue according to claim 3 wherein the reactive members of the first specific binding pair is an azide and the complementary reactive member of the first specific binding pair is an alkyne.

6. The method for adhering a medical device to biological tissue according to claim 3 wherein the reaction is catalyzed by metal to activate an alkyne and an azide for [3+2] cycloaddition.

7. The method for adhering a medical device to biological tissue according to claim 3 wherein the reaction involves a cyclooctyne reagent and an azide for [3+2] cycloaddition.

8. The method for adhering a medical device to biological tissue according to claim 2 wherein the members of the first specific binding pair are thiols and alkenes.

9. The method for adhering a medical device to biological tissue according to claim 2 wherein the members of the first specific binding pair are dienes and alkenes.

10. The method for adhering a medical device to biological tissue according to claim 2 wherein the tissue is provided with complementary reactive members of the first specific binding pair by applying a mixture or an aerosol containing the complementary reactive members to the tissue, the complementary reactive members being conjugated to a linker adapted to link the complementary reactive members to the tissue.

11. The method for adhering a medical device to biological tissue according to claim 10 wherein the complementary reactive members are attached to the tissue via an RGD linker.

12. The method for adhering a medical device to biological tissue according to claim 10 wherein the complementary reactive members are attached to the tissue via a ligand-receptor linkage.

13. The method for adhering a medical device to biological tissue according to claim 12 wherein the complementary reactive members are conjugated to a linker selected from the group consisting of antibody, Fab, F(ab')$_2$, Fv, single chain antibody (SCA) and single complementary-determining region (CDR).

14. The method for adhering a medical device to biological tissue according to claim 10 wherein the linker is degraded by hydrolysis or enzymatic action.

15. The method for adhering a medical device to biological tissue according to claim 10 wherein the ligand binds to a receptor selected from the group consisting of peptides, oligosaccharides, oligonucleotides and lipids.

16. The method for adhering a medical device to biological tissue according to claim 1 wherein the bifunctional adhesive composition is a hydrogel made of a polymer selected from the group consisting of polysaccharides, mucopolysaccharides, polyaminoacids, proteins, collagen-hydroxyethyl methacrylate (HEMA), polyphosphazines, polyphosphoesters, poly(ethylene glycol), poly(ethylene oxide), poly(vinyl alcohol), polyvinylpyrrolidone, polyethyloxazoline, poly (ethylene oxide-co-propylene oxide) block copolymers, poly(glycolic acid)-poly(ethylene glycol)-poly(glycolic acid) (PGA-PEG-PGA) block copolymers, PGA-PEG diblock copolymers, PEG-oligoglycolylacrylates, polyacrylonitriles (PAN), carboxy alkyl celluloses, poly($\alpha$-hydroxy) acids, polylactones, polycaprolactones, polyanhydrides, polyorthoesters, polydioxanone, polystyrene, and combinations thereof.

17. The method for adhering a medical device to biological tissue according to claim 16 wherein the mucopolysacharrides are selected from the group consisting of hyaluronic acid, dextran, heparin sulfate, chondroitin sulfate, heparin, agar, starch, and alginate; the proteins are selected from the group consisting of fibronectin, gelatin, collagen, fibrin, pectins, albumin, ovalbumin, and polyamino acids; the carboxy alkyl celluloses are selected from the group consisting of carboxymethyl cellulose and partially oxidized cellulose; poly($\alpha$-hydroxy) acids selected from the group consisting of poly(glycolic acid), poly(D,L-lactic acid), poly(L-lactic acid), and terpolymers of DL-lactide and glycolide; and polylactones selected from the group consisting of poly($\epsilon$-caprolactone), poly($\delta$-valerolactone) and poly($\gamma$-butyrolactone), $\epsilon$-caprolactone copolymerized with polyesters.

18. The method for adhering a medical device to biological tissue according to claim 1 wherein the bifunctional adhesive composition includes a polymer selected from the group consisting of polycarbonates, polyolefins, polymethacrylates, polystyrenes, polyamides, polyurethanes, poly(ethylene terephthalate), poly(lactic acid), poly(glycolic acid), polyhydroxybutyrate, polydioxanones, poly(phosphazine), polyesters, polyacrylamides, cellulose esters, fluoropolymers, vinyl polymers, silk, collagen, chitin, chitosan, chondroitin sulfate, glycosaminoglycans, poly(hydroxyethyl methacrylate), polyvinylpyrrolidone, poly(acrylic acid), polyacetate, polycaprolactone, polypropylene, poly(amino acids), copoly (ether-esters), poly(alkylene oxalates), poly iminocarbonates, polyoxaesters, polyorthoesters, polyphosphazenes, polypeptides and combinations thereof.

19. The method for adhering a medical device to biological tissue according to claim 1 wherein the medical device is selected from the group consisting of scaffold, adhesion barrier, patch matrix, plug, bandage, mesh and prosthetic device.

20. The method for adhering a medical device to biological tissue according to claim 1 wherein the bifunctional adhesive composition is a liquid which is applied to the tissue.

21. The method for adhering a medical device to biological tissue according to claim 1 wherein the bifunctional adhesive composition is a preformed layer which is applied to the tissue.

22. The method for adhering a medical device to biological tissue according to claim 1 wherein the bifunctional adhesive composition is applied to the device before contacting with the tissue.

23. The method for adhering a medical device to biological tissue according to claim 1 wherein the bifunctional adhesive composition is applied to the tissue before contacting with the device.

24. The method for adhering a medical device to biological tissue according to claim 2 wherein the members of the second specific binding pair are alkynes and azides.

25. The method for adhering a medical device to biological tissue according to claim 24 wherein the reactive member of the second specific binding pair is an alkyne and the complementary reactive member of the second specific binding pair is an azide.

26. The method for adhering a medical device to biological tissue according to claim 24 wherein the reactive members of the second specific binding pair is an azide and the complementary reactive member of the second specific binding pair is an alkyne.

27. The method for adhering a medical device to biological tissue according to claim 24 wherein the reaction is catalyzed by metal to activate an alkyne and an azide for [3+2] cycloaddition.

28. The method for adhering a medical device to biological tissue according to claim 24 wherein the reaction involves a cyclooctyne reagent and an azide for [3+2] cycloaddition.

29. The method for adhering a medical device to biological tissue according to claim 2 wherein the members of the second specific binding pair are thiols and alkenes.

30. The method for adhering a medical device to biological tissue according to claim 2 wherein the members of the second specific binding pair are dienes and alkenes.

* * * * *